United States Patent [19]

Colditz

[11] 4,155,254

[45] May 22, 1979

[54] VOLUME AND DENSITY INDICATOR SYSTEM FOR LIQUIDS IN TANKS

[75] Inventor: Eugene F. Colditz, Huntington Beach, Calif.

[73] Assignee: Kaiser Aerospace & Electronics Corp., Irvine, Calif.

[21] Appl. No.: 853,263

[22] Filed: Nov. 21, 1977

[51] Int. Cl.² ............................................. G01N 9/12
[52] U.S. Cl. ......................................... 73/447; 73/311
[58] Field of Search ................. 73/444, 445, 447, 451, 73/452, 291, 301, 305, 308, 309, 311, 319, 313, 322; 200/84 C

[56] References Cited

U.S. PATENT DOCUMENTS

| 533,153 | 1/1895 | Willard | 73/447 |
|---|---|---|---|
| 2,771,774 | 11/1956 | Fornasieri | 73/319 |
| 2,834,211 | 5/1958 | Samaritano | 73/322 |
| 3,921,461 | 11/1975 | Layton | 73/447 |
| 3,992,941 | 11/1976 | McGoldrick | 73/319 |

Primary Examiner—Stephen A. Kreitman

[57] ABSTRACT

A liquid storage tank is provided with an internal fixed support tube. Magnet-bearing liquid level and liquid density indicator floats are concentrically related to the fixed support tube externally thereof. Concentrically related, magnet-bearing indicator tubes are movably disposed within the fixed support tube and furnish liquid level and liquid density readout information when their respective magnets become magnetically latched with the float magnets.

3 Claims, 1 Drawing Figure

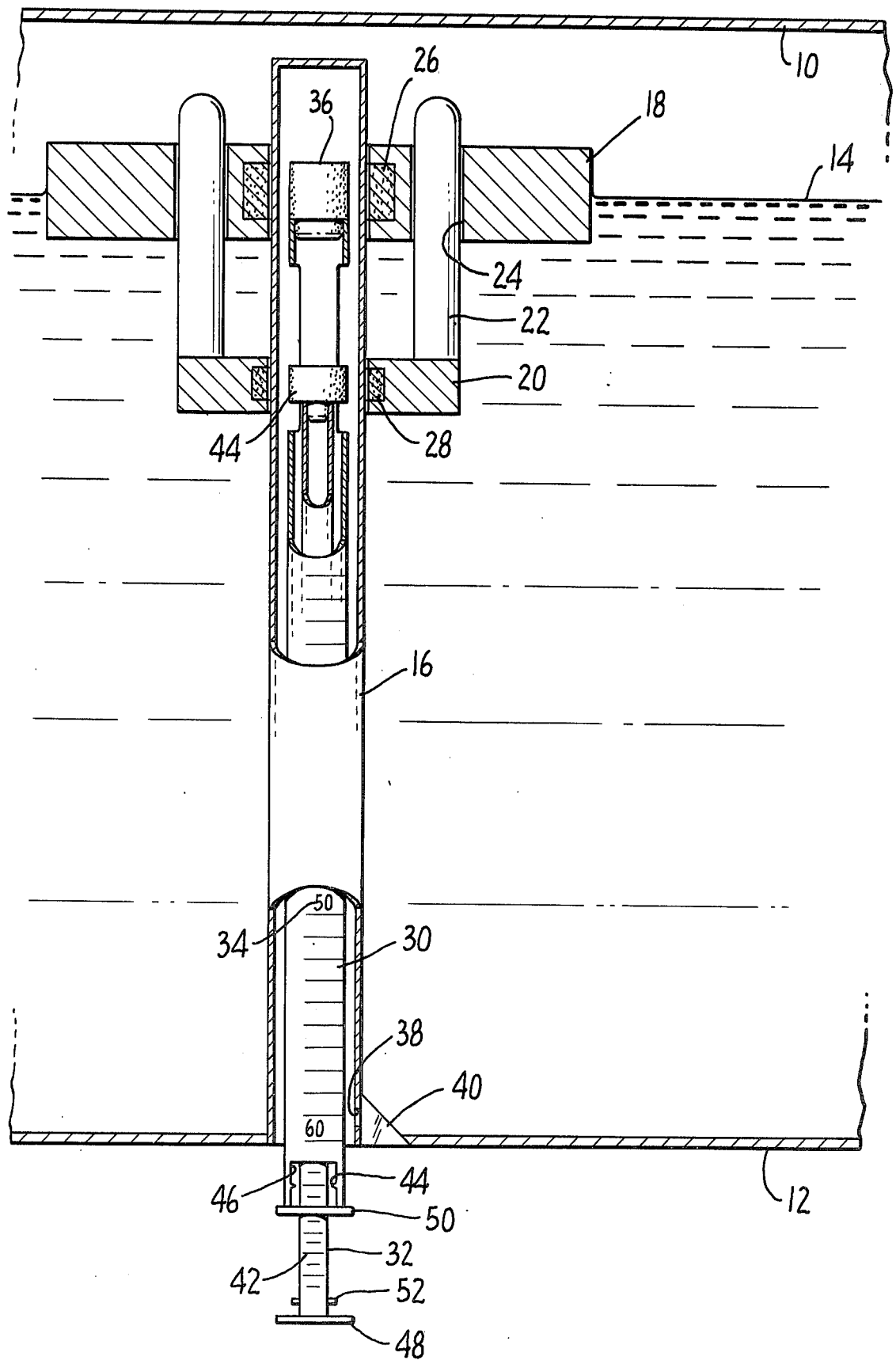

VOLUME AND DENSITY INDICATOR SYSTEM FOR LIQUIDS IN TANKS

BACKGROUND OF THE INVENTION

Present day jet aircraft use a variety of propellents which have a varying density as they are compounded by the refineries. This, together with atmospheric temperature changes, can result in a wide density variation of fuel. It is desirable to provide a fuel volume gauging system in order that a reliable determination of actual weight of the fuel in the tank may be made. Two aspects are required; one, the liquid level, which provides a volumetric indication in the tank, and two, the density of the liquid which occupies that volume.

The prior art known to applicant consists of U.S. Pat. Nos. 1,526,850, 2,500,348, 2,620,661, 2,834,211, 3,154,946, 3,407,660, 3,437,771 and 3,572,122.

SUMMARY OF THE INVENTION

The essential object of the invention is to provide an improved aircraft fuel tank indicator system adapted to furnish volume and density readings for the fuel within the tank.

Other objects and advantages of the invention will be apparent from the following description taken in conjunction with the drawing forming part of this specification which consists of a semi-schematic view partly in elevation and partly in section of the subject fuel level and density indicator.

In the drawing, 10 indicates the top of a wing-contained fuel tank, 12 indicates an outer wing surface, and 14 indicates the level of the fuel within the tank.

Positioned for vertical movement about a fixed support tube 16 are a fuel level indicator float 18 and a fuel density indicator float 20, the latter being provided with a plurality of guide members 22 which extend into guideways 24 formed in float 18. An annular magnet 28 is carried by float 20.

The float 18 is relatively large and it rests on the top 14 of the fuel in the tank, being relatively insensitive to the range of change of fuel density. The position of the float 20, however, within the fuel tank varies with respect to the position of the float 18 as a function of the density of the fuel, being located deeper in the fuel in proportion to the decrease in density of the fuel.

Supported for sliding movement within the support tube 16 are concentric tubes 30 and 32. Tube 30 is provided with indicia 34 whereby a reading for the location of fuel level 14 may be obtained. Tube 30 is provided at its upper end with a magnet 36 which upon being magnetically latched or coupled with magnet 26 positions the correct readout value for fuel level 14 adjacent a viewing port 38 in tube 16 for reading through prism 40.

Tube 32 is provided with density value indicia 42. Tube 32 is provided at its upper end with a magnet 44 which upon being magnetically latched or coupled with magnet 28 positions the appropriate density readout value on tube 32 between pointers 44 within view window 46 provided at the lower end of tube 30.

The tubes 30 and 32 are returned to storage position by moving the tube 32 upwardly until the flange 48 carried thereby engages the lower end 50 of tube 30. The tubes 30 and 32 are then secured together by means comprising latch pins 52 by turning the tube 32 through a quarter turn relative to tube 30. The two tubes are then pushed upwardly into the fixed tube 16 and secured in storage position by fastening a closure plug, not shown, into the lower end of the tube 16.

It is to be pointed out that the apparatus is readily adaptable through the provision of electronic means to indicate the liquid level value and the density value and to transmit these values to a site remote from the fuel tank proper.

What is claimed is:

1. Apparatus for determining the level and density of a liquid within a tank comprises a vertically disposed fixed tube positioned within the tank, a first float slidably mounted on said tube and adapted to float on the surface of the liquid within the tank, a second float slidably mounted on said tube and adapted to be immersed in said liquid to a depth which is inversely proportional to the density of said liquid, a pair of inner and outer concentric tubes disposed within said fixed tube for independent vertical movement with respect to each other, first complemental magnetic means carried by said first float and one of said concentric tubes adapted to be coupled through vertical movement of said one tube, second complemental magnetic means carried by said second float and the other of said concentric tubes adapted to be coupled through vertical movement of said other tube, a liquid level scale on said one tube and indicator means associated therewith to indicate a value thereon corresponding to the level of the liquid within the tank, and a density scale on said other tube and indicator means associated therewith to indicate a value thereon corresponding to the density of the liquid within the tank.

2. The apparatus of claim 1, said first complemental magnetic means being carried by said first float and the outer concentric tube, and said seconc complemental magnetic means being carried by said second float and the inner concentric tube.

3. The apparatus of claim 1 including a plurality of vertically disposed guide members carried by said second float extending into guide openings formed in said first float.

* * * * *